US00PP29714P3

(12) United States Plant Patent
Fraser

(10) Patent No.: US PP29,714 P3
(45) Date of Patent: Sep. 25, 2018

(54) ***CORDYLINE* PLANT NAMED 'PASO DOBLE'**

(50) Latin Name: *Cordyline australis*
Varietal Denomination: Paso Doble

(71) Applicant: Peter John Fraser, Waikato (NZ)

(72) Inventor: Peter John Fraser, Waikato (NZ)

( * ) Notice: Subject to any disclaimer, the term of this patent is extended or adjusted under 35 U.S.C. 154(b) by 27 days.

(21) Appl. No.: 15/530,002

(22) Filed: Nov. 16, 2016

(65) Prior Publication Data

US 2018/0139882 P1 May 17, 2018

(51) Int. Cl.
*A01H 5/12* (2018.01)

(52) U.S. Cl.
USPC ..... Plt./383
CPC ..... *A01H 5/12* (2013.01)

(58) Field of Classification Search
USPC ..... Plt./383
See application file for complete search history.

*Primary Examiner* — Keith O Neal Robinson

(57) ABSTRACT

A new cultivar of *Cordyline* plant named 'Paso Doble' that is characterized by leaves that are linear in shape, upright and dark red in color with dark pink margins.

1 Drawing Sheet

Botanical classification: *Cordyline australis.*
Variety denomination: 'Paso Doble'.

BACKGROUND OF THE INVENTION

The present invention relates to a new and distinct cultivar of *Cordyline australis* and is hereinafter referred to by the cultivar name 'Paso Doble'. The new *Cordyline* is the product of a planned breeding program conducted by the inventor in Kihikihi, Waikato, New Zealand. The objective of the breeding program is to create new *Cordyline* cultivars with attractive foliage colors. 'Paso Doble' originated from a crossing in 2006 of the female or seed parent *Cordyline* 'Red Fountain' (not patented) and the male or pollen parent *Cordyline* 'Albertii' (not patented). The resulting seeds were subsequently planted and grown. The cultivar 'Paso Doble' was selected by the inventor in the 2010 as a single plant within the progeny of the stated cross in Kihikihi, Waikato, New Zealand. Asexual reproduction of the new cultivar 'Paso Doble' first occurred by tissue culture in 2013 in Auckland, New Zealand. Since that time, under careful observation, the unique characteristics of the new cultivar have been uniform, stable and reproduced true to type in successive generations of asexual reproduction.

SUMMARY OF THE INVENTION

The new *Cordyline* 'Paso Doble' is distinguished from other known varieties of *Cordyline*, by the following characteristics:

1. *Cordyline* 'Paso Doble' exhibits leaves that are upright.
2. *Cordyline* 'Paso Doble' exhibits linear shaped leaves.
3. *Cordyline* 'Paso Doble' exhibits leaves that are dark red with dark pink margins.

The closest comparison cultivars are the parent plants *Cordyline* 'Red Fountain' and *Cordyline* 'Albertii'. 'Paso Doble' is distinguishable from the female parent 'Red Fountain' by the following characteristics:

1. 'Paso Doble' exhibits upright leaves. The leaves of 'Red Fountain' are more arching.
2. 'Paso Doble' exhibits leaves that are dark red with dark pink margins. The leaves of 'Red Fountain' are red.

'Paso Doble' is distinguishable from the male parent 'Albertii' by the following characteristics:

1. 'Paso Doble' exhibits leaves that are dark red with dark pink margins. The leaves of 'Albertii' are green with yellow margins.

'Paso Doble' can also be compared to Cordyline 'Zumba' (U.S. Plant Pat. No. 27,515). 'Paso Doble' is distinguishable from 'Zumba' by the following characteristics:

1. 'Paso Doble' exhibits erect upright leaves. The leaves of 'Zumba' are outwardly arching.
2. 'Paso Doble' exhibits leaves that are dark red with dark pink margins. The leaves of 'Zumba' are bright pink with deep red margins.

BRIEF DESCRIPTION OF THE DRAWINGS

The accompanying color photograph illustrates the distinguishing characteristics of the new cultivar 'Paso Doble'. The photograph shows an overall view of a 2 year old plant. All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Cordyline* cultivar named 'Paso Doble'. Data was collected in Kihikihi, Waikato, New Zealand from 2 year old plants. The plants were grown outdoors in 17 cm. diameter containers. The time of year was Winter in the Southern Hemisphere. The temperatures ranged from 2 to 15 degrees Centigrade during the day and from −2 to 10 degrees Centigrade at night. Phenotypic differences may be observed with variations in environmental, climatic, and cultural conditions, without however, any difference in genotype. Color determinations are in accordance with The 2007 Royal Horticultural Society Colour Chart except where general color terms of ordinary dictionary significance are used. The growing requirements are similar to the species.

Botanical classification: *Cordyline australis* 'Paso Doble'.
Common name: Cabbage Tree.

Parentage: 'Paso Doble' resulted from the crossing of the female or seed parent *Cordyline* 'Red Fountain' and the male or pollen parent *Cordyline* 'Albertii'.
Type: Ornamental perennial.
Container size: 17 cm. diameter.
Growth rate: Moderate.
Overall shape: Upright to semi-erect, broadly inverted triangle.
Habit: Upright.
Height: Average 1.1 m. in height.
Spread: Average 1.0 m. in width.
Low temperature tolerance: −5 degrees Centigrade.
High temperature tolerance: 30 degrees Centigrade.
Propagation method: Tissue culture.
Time to initiate roots: 6 months.
Time to produce a rooted liner: 2 months.
Crop time: 14 months.
Vigor: Moderate.
Root system: Fibrous.
Root color: N155A.
Stem:
*Texture*.—Smooth.
*Dimensions*.—Average 3.6 cm. in diameter and 5.1 cm. in length.
*Color*.—200C.
*Basal shoots*.—Absent.
Foliage:
*Arrangement*.—Whorled.
*Orientation*.—Initially erect then outwardly arching.
*Average number of leaves per plant*.—64.
*Compound or single*.—Single.
*Leaf attachment*.—Sessile.
*Leaf shape*.—Linear.
*Leaf dimensions*.—Average 50 cm. in length and 20 mm. in width.
*Leaf apex*.—Acute.
*Leaf base*.—Attenuate.
*Leaf margins*.—Entire.
*Leaf texture*.—(Both surfaces): Smooth.
*Leaf glossiness*.—(Both surfaces): Slightly glossy.
*Leaf pubescence*.—Absent.
*Leaf curvature*.—Absent.
*Leaf color of young leaves* (*upper surface*).—N186C, margins 59B.
*Leaf color of young leaves* (*lower surface*).—N186C, margins 184B.
*Leaf color of mature leaves* (*upper surface*).—N186C, margins 59B.
*Leaf color of mature leaves* (*lower surface*).—N186C, margins 184B.
*Venation pattern*.—Parallel.
*Vein color* (*upper surface*).—70C.
*Vein color* (*lower surface*).—61A.
*Pinching*.—Removal of young plant tips is not required.
*Durability of foliage to stress*.—High.
*Leaf fragrance*.—Absent.
Flower production: No flowers have been produced by 'Paso Doble' to date.
Fruit and seed production: Has not been observed.
Disease and pest resistance: Has not been observed.

The invention claimed is:

1. A new and distinct variety of *Cordyline* plant named 'Paso Doble' as described and illustrated.

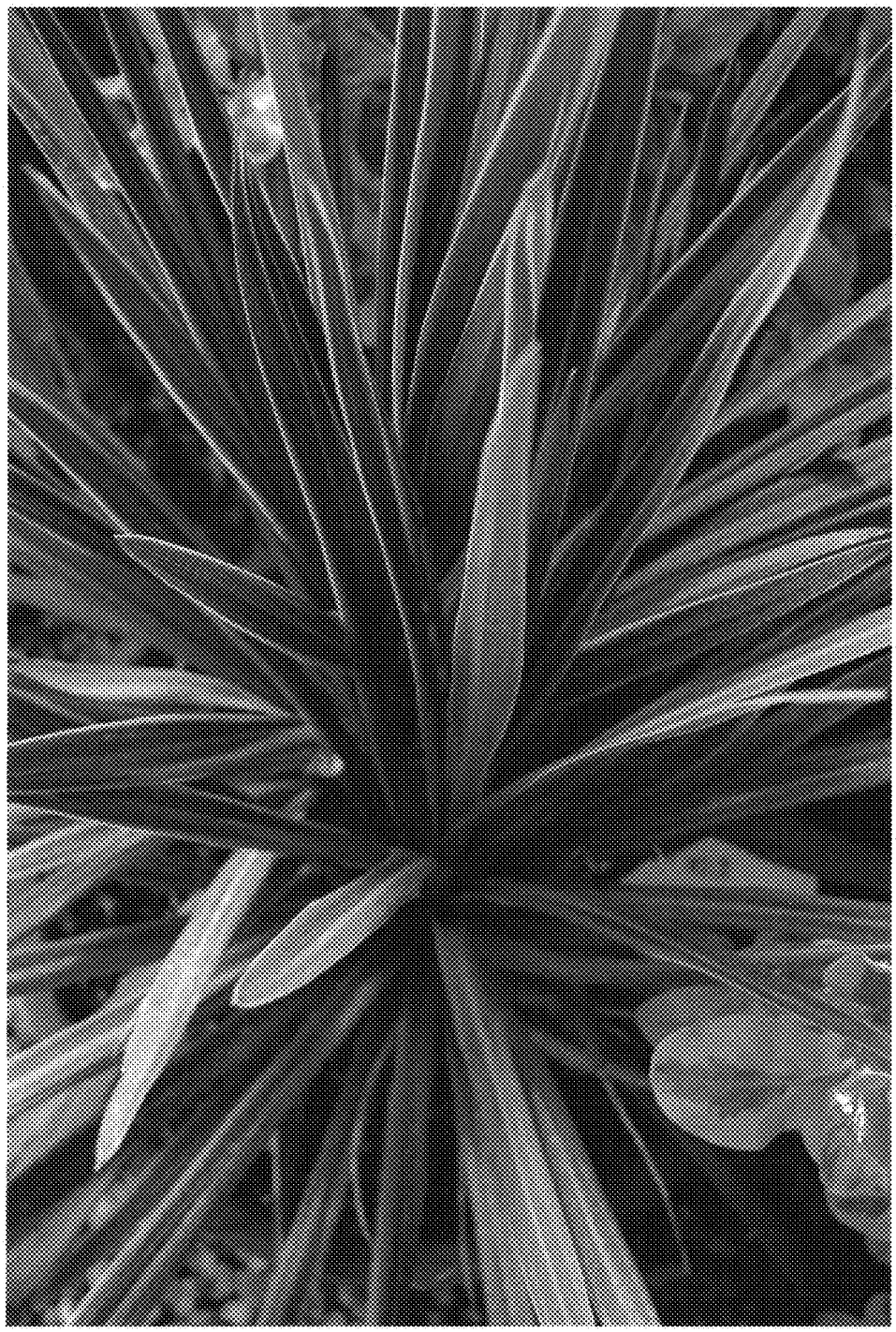

* * * * *